United States Patent [19]

Allen

[11] Patent Number: 5,111,703

[45] Date of Patent: May 12, 1992

[54] LIQUID ASPIRATING PIPETTE AND DISPENSING SYSTEM

[75] Inventor: Terry W. Allen, Rochester, N.Y.

[73] Assignee: Eastman Kodak Company, Rochester, N.Y.

[21] Appl. No.: 580,041

[22] Filed: Sep. 10, 1990

[51] Int. Cl.⁵ .............................. G01N 1/14; B01L 3/02
[52] U.S. Cl. .............................. 73/864.11; 73/864.14; 73/864.16
[58] Field of Search ........... 73/864.11, 864.14, 864.18, 73/864.16

[56] References Cited

U.S. PATENT DOCUMENTS

| | | | |
|---|---|---|---|
| 3,248,950 | 5/1966 | Pursell et al. | 73/864.18 |
| 4,327,595 | 5/1982 | Schultz | 73/864.12 |
| 4,435,989 | 3/1984 | Meyer et al. | 73/864.18 X |
| 4,487,081 | 12/1984 | De Vaughn et al. | 73/864.16 X |
| 4,489,618 | 12/1984 | Meyer | 73/864.16 |
| 4,567,780 | 2/1986 | Oppenlander et al. | 73/864.16 |
| 4,671,123 | 6/1987 | Magnussey, Jr. et al. | 73/864.16 |

FOREIGN PATENT DOCUMENTS 624312  7/1981  Switzerland .................... 73/864.14

Primary Examiner—Tom Noland
Attorney, Agent, or Firm—Dressler, Goldsmith, Shore, Sutker & Milnamow, Ltd.

[57] ABSTRACT

A manually operable, liquid aspirating pipette, and associated dispensing apparatus, are disclosed. The pipette includes a manually operable aspirator arrangement which permits collection and aspiration of a liquid sample. A pull-back mechanism is provided to facilitate convenient introduction of air into the pipette subsequent to aspiration of the liquid sample. Notably, the pipette includes a secondary actuating member which permits operation of the pipette by the associated dispensing apparatus. Thus, after aspiration of a liquid sample, the pipette may be positioned in the dispensing apparatus, with the apparatus operated to provide controlled, metered dispensing of the sample in the desired manner.

6 Claims, 2 Drawing Sheets

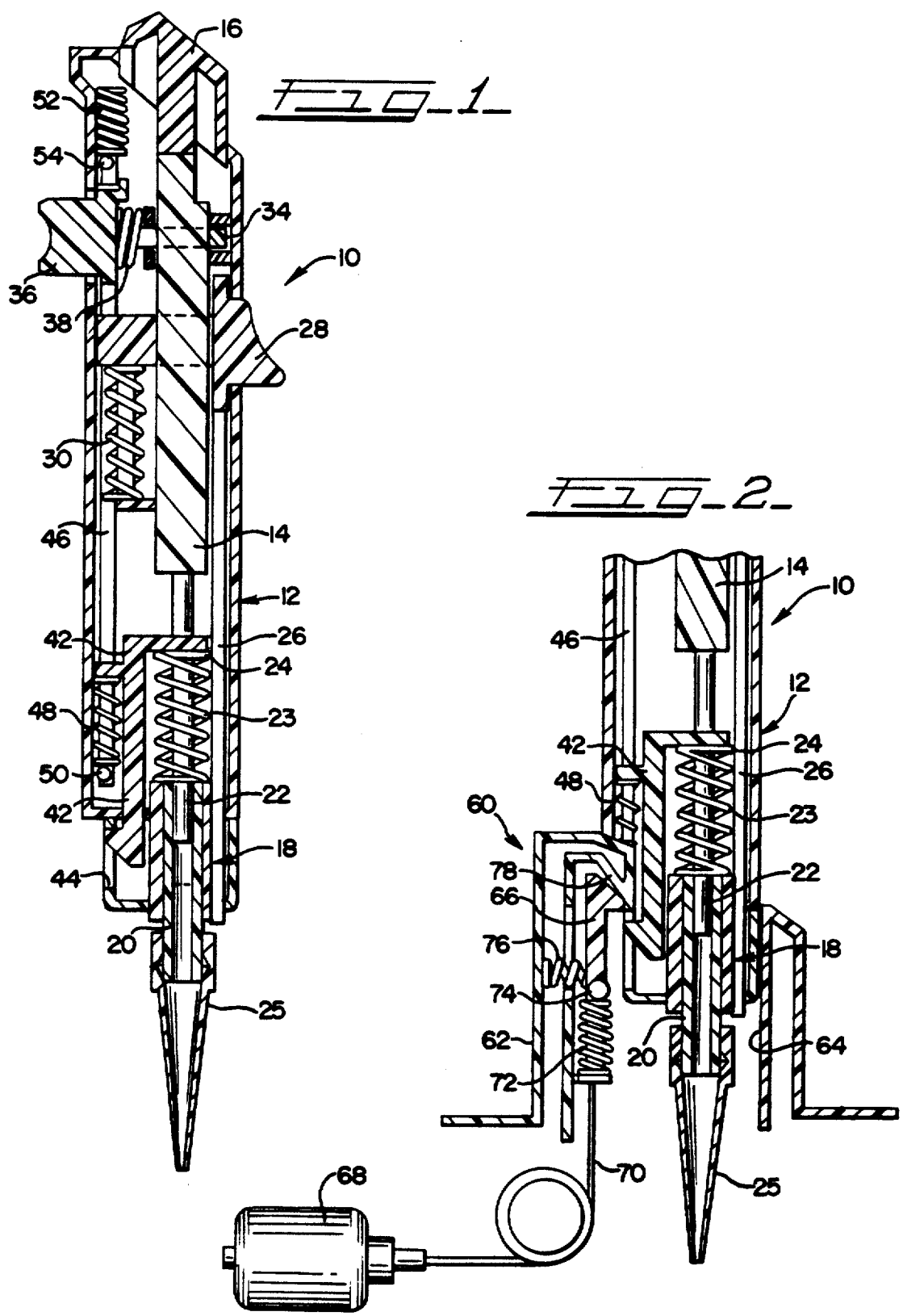

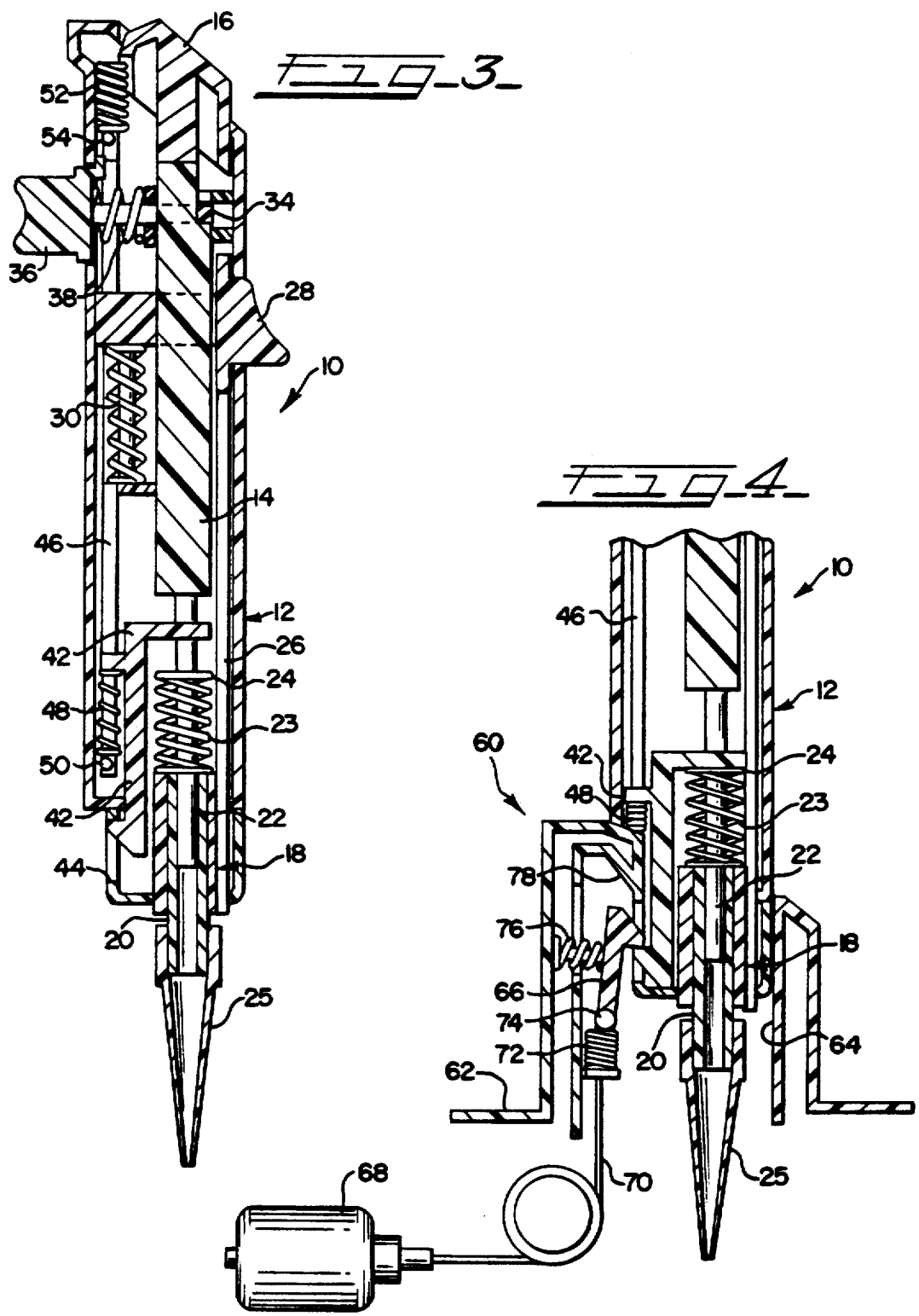

LIQUID ASPIRATING PIPETTE AND DISPENSING SYSTEM

TECHNICAL FIELD

The present invention relates to devices for aspirating and dispensing liquid samples for test analysis and the like, and more particularly to a dispensing system including a manually operable aspirating pipette, and an associated dispensing apparatus configured to receive the pipette for automatic metered dispensing of its contents.

BACKGROUND OF THE INVENTION

Chemical analysis or other testing of liquid samples typically requires collection of such samples from containers for subsequent dispensing on chemistry slides or the like for analysis. Pipettes and similar aspirating devices, either manual or automatic in nature, are ordinarily employed for this purpose.

Depending upon the nature of the analysis to be performed, precise volumetric control of the liquid samples may be required. Samples to be subjected to analysis, control substances, and calibrator fluids frequently must be dispensed in a controlled manner, at predetermined volumes and dispensing rates.

A number of factors must be considered in order for accurate chemical analysis to be achieved. Among these are accurate volumetric aspiration of the liquid sample, minimal liquid perfusion, minimal exposure of the sample to air, minimal drop formation about the exterior of the pipette tip, and control of the dispensing rate.

A typical pipette mechanism for this purpose includes a movable piston arranged within an associated cylinder. By submersion of the free end of the cylinder into a fluid sample, vacuum created within the cylinder by relative movement of the piston causes the liquid to flow into the cylinder, under the influence of external barometric pressure. This flow is governed by the volumetric movement of the piston, as well as the vapor pressure of the liquid, the liquid surface tension, and capillary action. The piston and cylinder arrangement is then removed from the liquid so that the sample can be dispensed as desired.

Because sample sizes can be quite small in volume, a significant quantity of the liquid within the pipette cylinder can be lost if a drop is allowed to form on the free end of the device, thereby compromising accuracy. Such drop formation can result from movement of the piston within the cylinder, fluid adhesion to the outside of the device, thermal and vapor pressure changes within the cylinder head volume above the liquid, and changes in the barometric environment.

A reduction in fluid losses can be achieved by preventing a drop from forming once the pipette is removed from the sample container. In particular, drop formation can be prevented by causing a small air pocket to be formed at and within the open end of the pipette by sucking back the liquid sample with a small additional backward movement of the piston. The small air pocket compensates for cylinder head expansion, minimizes exposure of the sample to the atmosphere by reduction in the exposed surface area, and desirably prevents the formation of a drop on the end of the device that can be inadvertently removed through physical contact or the like.

During dispensing of the sample for analysis, it is ordinarily necessary to achieve accurate sample volume control, accurate drop placement, and controlled dispensing rates in order to achieve precision during subsequent analysis. Since some analysis requires several liquids to be sequentially applied to a single slide, the differing viscosity of the liquids, and their chemical composition may require different dispensing rates, or like variations during analysis.

The present invention provides a liquid aspirating and dispensing system which is desirably suited to facilitate efficient, accurate, and automated liquid sample handling for subsequent analysis and the like.

SUMMARY OF THE INVENTION

The present liquid aspirating and dispensing system includes a manually operable liquid aspirating pipette, and an associated automatic dispensing apparatus. The pipette is desirably configured for convenient manual operation for aspirating and collecting a liquid sample, with the device arranged to conveniently permit subsequent aspiration of air to minimize any loss of the liquid sample, thus facilitating accurate use. The associated dispensing apparatus is configured to removably receive the pipette therein, with the apparatus including an arrangement for automatically operating the pipette to permit precise, metered dispensing of the liquid sample.

A manually operable liquid aspirating cassette in accordance with the present invention comprises a pipette housing, and an actuating linkage extending within the housing which is manually movable relative thereto.

The pipette further comprises a liquid aspirator positioned generally within the housing, with the aspirator operatively connected to the actuating linkage for movement between first and second positions. The aspirator is operable to aspirate liquid during movement from the second position to the first position, and is operable to dispense liquid during movement from the first position to the second position.

Biasing means operatively connected to the aspirator bias the aspirator from the second position into the first position.

A manually operable pull-back mechanism is operatively connected to the aspirator. The pull-back mechanism is operable to releaseably retain the aspirator in a third position, intermediate the first and second positions, during movement of the aspirator from the second position to the first position. Manual operation of the pull-back mechanism releases the aspirator to permit movement from the third position to the first position by the biasing means.

The pipette thus permits a liquid sample to be aspirated during movement of the aspirator from the second position to the third position, followed by aspiration of air during movement of the aspirator from the third position to the first position by release of the pull-back mechanism.

In accordance with the illustrated embodiment, the liquid aspirating pipette includes a generally elongated, hollow pipette housing, and the actuating linkage extending within the housing for manual movement relative thereto.

The pipette further includes a liquid aspirator positioned generally within the housing at the lower end thereof. In the illustrated embodiment, the aspirator comprises an aspirator cylinder defining an aspirator chamber, with the cylinder fixedly mounted on the pipette housing. The aspirator further includes an aspirator piston operatively connected to the actuating linkage for movement relative to the aspirator cylinder for aspiration of liquid.

The aspirator is operable, by movement of the piston thereof, between first and second positions. Liquid is aspirated and drawn into the pipette during movement from the second position to the first position, with the device being operable to dispense liquid during movement from the first position to the second position. A biasing spring is preferably operatively connected to the aspirator for biasing the mechanism from the second position into its first position.

To facilitate accurate liquid sampling, the present pipette includes a manually operable pull-back mechanism which is operatively connected, via the actuating linkage, to the liquid aspirator. In the illustrated embodiment, the pull-back mechanism comprises a latch member which is movable generally laterally of the pipette housing and the actuating linkage between a release position and a latched position. A latch biasing spring urges the latch member into the latched position.

The pull-back mechanism is operable to releasably retain the liquid aspirator in a third position, which is intermediate the first and second positions thereof, during movement of the aspirator from the second position toward the first position. The latch biasing spring acts to automatically effect this engagement, so that subsequent manual operation of the pull-back mechanism releases the actuating linkage, and thus the aspirator, to permit movement thereof from the third position back to the first position, under the influence of the associated biasing spring.

This arrangement permits a liquid sample to be aspirated during movement of the aspirator from the second position back to the latched, third position. By release of the pull-back mechanism, air is then aspirated during movement of the aspirator from the third position back to the first position.

In accordance with the present system, an automated dispensing apparatus is provided which is configured to receive the pipette for automated operation thereof. The pipette includes a secondary actuating member operatively connected to the aspirator for moving the aspirator between its first and second positions. In the preferred form, the pipette housing defines an access opening for the secondary actuating member for operation by the associated dispensing apparatus.

The dispensing apparatus, in turn, includes a metering member which is engageable with the secondary actuating member of the pipette. The dispensing apparatus includes a driver for driving the metering member, with the apparatus operable to move the aspirator of the pipette from its first position to its second position, thereby providing automated dispensing of a liquid sample from the pipette. Suitable automatic controls can be provided for the driver of the dispensing apparatus to provide programmed, metered dispensing of a liquid sample at desired rates and volumes.

To facilitate convenient operation, the pipette preferably includes an arrangement which locksout or disables the manual pull-back mechanism during operation of the pipette by the dispensing apparatus. A lock-out arrangement is operatively connected with the secondary actuating member of the pipette, and the pull-back mechanism. The lock-out arrangement operates to prevent the pull-back mechanism from retaining the pipette aspirator in the third, intermediate position when the secondary actuating member is operated (by the dispensing apparatus) to move the aspirator. This permits movement of the aspirator from its second position fully back to its first position without being releasably retained in the latched, intermediate third position. Thus, after removal of the pipette from the dispensing apparatus, the pipette is ready for further sample aspiration.

Other features and advantages of the present invention will become readily apparent from the following detailed description, the accompanying drawings, and the appended claims.

BRIEF DESCRIPTION OF THE DRAWINGS

FIG. 1 is a side-elevational, diagrammatic view illustrating a manually operable liquid aspirating pipette embodying the principles of the present invention;

FIG. 2 is a fragmentary, diagrammatic view illustrating the pipette of FIG. 1 in place in an automated dispensing apparatus;

FIG. 3 is a cross-sectional view similar to FIG. 1 further illustrating the present pipette; and FIG. 4 is a view similar to FIG. 2 illustrating operation of the present pipette by the associated dispensing apparatus.

DETAILED DESCRIPTION

While the present invention is susceptible of embodiment in various forms, there is shown in the drawings and will hereinafter be described a presently preferred embodiment, with the understanding that he present disclosure is to be considered as an exemplification of the invention, and is not intended to limit the invention to the specific embodiment illustrated.

With reference now to the drawings, therein is illustrated a manually operable liquid aspirating pipette 10 embodying the principles of the present invention. While the pipette 10 can be configured only for manual use, the present invention contemplates that the pipette 10 be configured for both manual operation, as well as automatic operation in conjunction with an associated dispensing apparatus of the present invention.

The pipette 10 includes a generally elongated, hollow pipette housing 12 within which extends a generally elongated actuating linkage 14. An actuating button 16, projecting generally from the top of housing 12, is operatively connected to the linkage 14 and permits manual, generally axial movement of the linkage relative t the pipette housing.

The actuating linkage 14 is operatively connected with an aspirator 18 mounted generally at the lower extent of the pipette housing 12. In the illustrated embodiment, aspirator 18 includes an aspirator cylinder 20 fixedly mounted on the housing 12, and an aspirator piston 22 which is operatively connected to the actuating linkage 14 for movement relative to the cylinder 22 for aspiration of liquids into the cylinder.

The cylinder and piston arrangement can be appropriately sized for aspiration of liquid samples of the desired volume. While the piston and cylinder arrangement typically comprise metallic components, other aspects of the present pipette may be suitably and economically fabricated from plastic materials or the like. While the illustrated embodiment of the pipette 10 shows the aspirator 18 as comprising the above-described piston and cylinder construction, the aspirator may be otherwise configured, such as comprising a bellows-type aspirator mechanism, as is known in the art.

In the preferred embodiment, the pipette 10 further includes a biasing spring 23, which in the illustrated embodiment, comprises a compression coil spring held in captive relation on the piston 22 between a spring retainer 24 and the cylinder 20. By depressing the actuating button 16, the actuator linkage 14 acts in opposition to the biasing spring 23 to move the aspirator piston 22 from a first, generally raised or retracted position, to a second position. Convenient operation is thus facilitated, since the biasing spring 23 biases the aspirator piston 22 from its second position into the first position thereof (for creating a vacuum within the chamber defined by the cylinder 20), with movement of the actuating linkage, in opposition to the biasing spring, acting to dispense liquid from the pipette.

In the preferred form, the pipette 10 includes a replaceable hollow tip 25 releasably joined to the aspirator cylinder 20 of the aspirator 18. Liquid flows into and out of the aspirator tip attendant to operation of the aspirator 18, thus permitting convenient and accurate aspiration and dispensing of liquid samples. In order to facilitate replacement of the tip 25, the pipette 10 includes a manually operable tip ejector mechanism mounted generally within the housing 12, including a tip ejector rod 26 which is movable into engagement with the replaceable tip 25 to disconnect the tip from the aspirator cylinder 20. The ejector rod 26 is operated by an ejector button 28, with the rod 26 and the button 28 preferably biased away from the tip, to the position shown in FIG. 1, by an associated ejector biasing spring 30 operatively connected with the button 28. In accordance with the illustrated embodiment, the ejector biasing spring 30 can be mounted in captive relation between a portion of the ejector button 28 extending adjacent to or through the actuating linkage 14, and a portion of the housing 12 against which the spring 30 is seated.

In accordance with the present invention, it can be desirable to aspirate air into the tip 25 of the pipette, subsequent to the aspiration of a liquid sample, thus avoiding drop formation and minimizing the exposed surface area of the sample. Accordingly, the pipette 10 includes a manually operable pull-back mechanism which acts to releasably retain the actuator linkage 14 during the upstroke or retraction of the aspirator piston 22. The pull-back mechanism includes a pull-back latch member 34 which is movable generally laterally of the pipette housing 12 and generally laterally of the actuating linkage 14. The latch member is movable between a release position, shown in FIG. 1, and a latched position, shown in FIG. 3, wherein the latch member engages a stepped portion of the actuating linkage to retain the actuating linkage against the action of biasing spring 23.

A pull-back button 36 is operatively connected with the latch member 34 for urging the latch member from its latched position toward its release position in opposition to an ejector biasing spring 30.

By this arrangement, the aspirator 18, and in particular, the aspirator piston 22, can be releasably retained in a third position which is intermediate the first retracted position and the second position thereof. In order to release the actuating member 14, and thus the aspirator piston 22, from this latched, third position, the pull-back button 36 is depressed, thereby disengaging the latch member 34 from the stepped region of the actuating linkage 14. The biasing spring 23 thereafter urges the aspirator piston 22 from the third latched position to the fully retracted, first position.

This arrangement permits the operator of the pipette to first depress the actuating button 16, thereby moving the piston 22 from its first position to its second position, and after placement of the tip 25 in the liquid to be sampled, release the button 16 whereupon the aspirator piston 22 moves upwardly from its second position During the downward movement of the actuating member, the pull-back latch member 34 automatically engages the stepped region of the actuating linkage, so that upon the return stroke, the aspirator piston is automatically retained in its third, intermediate position.

The operator then withdraws the tip of the pipette from the liquid being sampled, and depresses the pull-back button 36. This acts to disengage the latch member 34 from the actuating member 14, thereby permitting the continued upward movement of the actuator piston 22, under the influence of biasing spring 23, so that the piston moves from the third latched position, to its fully retracted, first position. A quantity of air is thus aspirated into the tip 25 beneath the liquid sample.

As will be further described, the present pipette is desirably configured for automatic dispensing of a liquid sample therein. It is desirable to lock-out or disable the pull-back mechanism, so that during automatic operation, the aspirator piston 22 can move fully from its second position back to its fully retracted, first position.

To facilitate the desired automatic dispensing, a secondary actuating member 42 is provided, which is operatively connected with the piston 22 of aspirator 18 at the spring retainer 24, with the actuating linkage 14 and piston 22 being movable relative to the member 42 attendant to operation of the linkage. In the illustrated embodiment, the pipette housing 12 defines an access opening 44 for the secondary actuating member 42 for operation of the actuating member 42 by the associated automatic dispensing apparatus.

The disablement of the pull-back mechanism is achieved by the provision of a lock-out rod 46 which is operatively connected with the secondary actuating member 42 and the pull-back button 36. Specifically, a compression spring 48 is held captive between the actuating member 42 and a suitable pin 50 on the lock-out rod 46. The upper end of the lock-out rod is operatively connected with a tension spring 5,, with an engagement pin 54 being positioned for engagement with the pull-back button 36, which engagement prevents the pull-back latch member 34 from moving into the stepped region of actuating linkage 14 under the influence of pull-back biasing spring 38.

The illustrated embodiment is configured such that the spring 48 exerts a higher spring force than the tension spring 52, thus permitting the lock-out rod 46 to move downwardly with the secondary actuating member 42 in opposition to the tension spring 52. Upon engagement and seating of the engagement pin 54 with the pull-back button 36, the spring 48 cooperates with the actuating member 42 and the lock-out rod 46 to provide a lost-motion mechanism, thereby permitting continued downward movement of the actuating member 42 relative to the lock-out rod 46.

With particular reference now to FIGS. 2 and 4, therein is diagrammatically illustrated the automated dispensing apparatus 60 of the present system. The dispensing apparatus 60 is configured to removably receive the pipette 10 for automated operation thereof, in particular, for automated metered dispensing of liquid from within aspirator 18 of the pipette.

Dispensing apparatus 60 includes a suitable housing 62 defining a pipette cavity 64 for receiving the lower end of pipette 10. A pawl-like metering member 66 is positioned in operative association with the pipette cavity 64 for cooperative engagement with secondary actuating member 42.

The dispensing apparatus 60 includes a driver 68, which may comprise a mechanical, electro-mechanical, pneumatic, or hydraulic device, which is operatively connected with the metering member 66 by a suitable drive linkage 70. The arrangement can include a return spring 72 operatively connected with the metering member 60. In the illustrated embodiment, the metering member includes a pivotal connection 74 joining the metering member to the drive linkage 70, with a biasing spring 76 urging the metering member 66 generally toward the cavity 64, thereby urging the metering member into engagement with the secondary actuating member 42 through the access opening 44 in the pipette housing. In the preferred embodiment, the housing 62 includes a cam surface 78 which cooperates with the metering member 66 for urging the metering member away from the cavity, thus facilitating insertion and removal of the associated pipette.

From the foregoing, the operation of the present system will be readily appreciated. The cooperating configuration of pipette 10 and the housing 62 of the dispensing apparatus, including the cavity 64, act to locate the pipette in a predetermined disposition generally within the housing 62. During insertion, the metering member 66 is generally in the position illustrated in FIG. 2, thus facilitating unencumbered insertion of the pipette.

To initiate automatic dispensing of the liquid sample from within the tip 25 of the pipette 10, the driver 68 is operated so that the metering member 66 is moved generally downwardly relative to housing 62. By this action, and under the influence of biasing spring 76, the metering member is urged into cooperative engagement with the secondary actuating member 42 of the pipette. Upon engagement of the metering member with the actuating member 42, continued operation of the driver effects dispensing of the liquid sample within the aspirator 18 of the pipette. Suitable automatic controls are preferably provided to facilitate dispensing at the desired rate, and dispensing of the desired liquid volumes.

As discussed above, downward movement of the secondary actuating member 42 acts to operate lock-out rod 46, thereby disabling the pull-back mechanism of the pipette during the return stroke of the dispensing system. This permits the dispensing apparatus to return the pipette piston 22 to its upwardmost, retracted first position for subsequent reuse by the operator without releasing the pull-back mechanism of the pipette. During the upward stroke, the metering member 66 cooperates with the cam surface 78 of the housing 62 so that member 66 returns to its generally retracted position relative to the cavity 62.

The present system can be provided in various configurations, depending upon the desired sampling and dispensing operations to be performed. While the present invention has been disclosed as including a single pipette cassette 10, the arrangement may be readily configured to include multiple pipettes operated in cooperation with each other. Releasable connection means can be provided in order to suitably connect plural ones of the pipettes together. The pipettes may be suitably configured for independent operation, or may be arranged to operate in ganged fashion for common aspiration and dispensing.

From the foregoing, it will be observed that numerous modifications and variations can be effected without departing from the true spirit and scope of the novel concept of the present invention. It is to be understood that no limitation with respect to the present disclosure is intended or should be inferred. The disclosure is intended to cover by the appended claims all such modifications as fall within the scope of the claims.

What is claimed is:

1. A manually operable liquid aspirating pipette, comprising:
   a pipette housing;
   an actuating linkage extending within said housing and being manually movable relative thereof;
   liquid aspirator means positioned generally within said housing and operatively connected to said actuating linkage for movement between first and second positions, said aspirator means being operable to aspirate liquid during movement from said second position to said first position, and operable to dispense liquid during movement from said first position to said second position;
   biasing means operatively connected to said aspirator means for biasing said aspirator means from said second position into said first position;
   manually operable pull-back means operatively connected to said aspirator means, said pull-back means being operable to releasably retain said aspirator means in a third position, intermediate said first and second positions, during movement of said aspirator means from said second position to said first position, so that manual operation of said pull-back means releases said aspirator means to permit movement from said third position to said first position by said biasing means;
   a secondary actuating member operatively connected to said aspirator means for moving said aspirator means between said first and second positions; and
   pull-back lock-out means operatively connected with said secondary actuating member and said pull-back means, said lock-out means operating to prevent said pull-back means from retaining said aspirator means in said third position thereof when said secondary actuating member is operated to move said aspirator means, to thereby permit movement of said aspirator means from said second position to said first position without being releasably retained in said third position,
   wherein said pipette permits a liquid sample to be aspirated during movement of said aspirator means from said second position to said third position, followed by aspiration of air during movement of said aspirator means from said third position to said first position by release of said pull-back means.

2. A manually operable pipette in accordance with claim 1, including
   lost-motion means operatively connecting said pull-back lock-out means to said secondary actuating member to permit movement of said secondary actuating member relative to said lock-out means after said lock-out means operates to prevent said pull-back means from retaining said aspirator means in said third position.

3. A liquid aspirating and dispensing system, comprising:
- a manually operable pipette including a pipette housing, an actuating linkage extending within said housing for manual movement relative thereto, and liquid aspirator means positioned generally within said housing,
- said aspirator means being operatively connected to said actuating linkage for movement between first and second positions, said aspirator means being operable to aspirate liquid during movement from said second position to said first position, and operable to dispense liquid during movement from said first position to said second position;
- said pipette further including a secondary actuating member operatively connected to said aspirator means for moving said aspirator means between said first and second positions; and
- an automated dispensing apparatus configured to removably receive said pipette for automated operation thereof, said dispensing apparatus including a metering member engageable with said secondary actuating member of said pipette, and means for driving said metering member, whereby said dispensing apparatus is operable to move said aspirator means from said first position to said second position for automated dispensing of a liquid sample from said pipette,
- wherein said dispensing apparatus defines a pipette cavity for releasably receiving said pipette, said apparatus including cam means for urging said metering member away from said cavity to facilitate insertion and removal of said pipette.

4. A liquid aspirating and dispensing system in accordance with claim 3, wherein
- said pipette includes manually operable pull-back means operatively connected to said aspirator means, said pull-back means being operable to releasably retain said aspirator means in a third position, intermediate said first and second positions, during movement of said aspirator means from said second position to said first position,
- said pipette further including pull-back lock-out means operatively connected with said secondary actuating member and said pull-back means, said lock-out means operating to prevent said pull-back means from retaining said aspirator means in said third position when said secondary actuating member is operated to move said aspirator means, to thereby permit movement of said aspirator means from said second position to said first position without being releasably retained in said third position.

5. A liquid aspirating and dispensing system in accordance with claim 4, wherein
- said pipette includes biasing means for biasing said aspirator means from said second position to said first position.

6. A liquid aspirating and dispensing system in accordance with claim 5, wherein
- said pull-back means comprises a latch member movable generally laterally of said housing and said actuating linkage between a release position and a latched position, and latch biasing means for urging said latch member into said latched position,
- said latch biasing means acting to automatically urge said latch member into said latched position during movement of said aspirator from said first position to said second position by movement of said actuating linkage, so that said latch member is thereby positioned to engage said actuating linkage to retain said aspirator means in said third position during movement from said second position toward said first position.

* * * * *

UNITED STATES PATENT AND TRADEMARK OFFICE
CERTIFICATE OF CORRECTION

PATENT NO. : 5,111,703
DATED : May 12, 1992
INVENTOR(S) : Terry W. Allen

It is certified that error appears in the above-identified patent and that said Letters Patent is hereby corrected as shown below:

Column 4, line 47          "t the" should be --to the--.

Column 6, line 47          "5,," should be --52,--.

Column 8, line 18          "thereof;" should be --thereto;--.

Signed and Sealed this

Twentieth Day of July, 1993

Attest:

MICHAEL K. KIRK

Attesting Officer      Acting Commissioner of Patents and Trademarks